US008862211B2

(12) United States Patent
Toledo et al.

(10) Patent No.: US 8,862,211 B2
(45) Date of Patent: Oct. 14, 2014

(54) APPARATUS AND METHOD FOR IDENTIFYING MYOCARDIAL ISCHEMIA USING ANALYSIS OF HIGH FREQUENCY QRS POTENTIALS

(71) Applicant: BSP Biological Signal Processing Ltd., Tel-Aviv (IL)

(72) Inventors: Eran Toledo, Tel Aviv (IL); Amir Beker, Rosh HaAyin (IL); Orna Bregman-Amitai, Tel-Aviv (IL)

(73) Assignee: BSP Biological Signal Processing Ltd., Tel-Aviv (IL)

( * ) Notice: Subject to any disclaimer, the term of this patent is extended or adjusted under 35 U.S.C. 154(b) by 0 days.

(21) Appl. No.: 14/022,258

(22) Filed: Sep. 10, 2013

(65) Prior Publication Data

US 2014/0031709 A1 Jan. 30, 2014

Related U.S. Application Data

(63) Continuation of application No. 12/375,544, filed as application No. PCT/IL2007/000971 on Aug. 2, 2007, now Pat. No. 8,538,510.

(60) Provisional application No. 60/821,268, filed on Aug. 3, 2006.

(51) Int. Cl.
*A61B 5/04* (2006.01)
*A61B 5/00* (2006.01)
*A61B 5/0472* (2006.01)

(52) U.S. Cl.
CPC .......... *A61B 5/04012* (2013.01); *A61B 5/6804* (2013.01); *A61B 5/7203* (2013.01); *A61B 5/746* (2013.01); *A61B 5/0472* (2013.01); *A61B 5/4884* (2013.01); *A61B 5/04014* (2013.01)
USPC .......................................... 600/509; 600/516

(58) Field of Classification Search
CPC ........ A61B 5/04041–5/04015; A61B 5/04012; A61B 5/04018; A62B 5/7303; A62B 5/4884; A62B 5/6804; A62B 5/0472; A62B 5/746
USPC ......................... 600/508–528; 607/4–5, 9, 14
See application file for complete search history.

(56) References Cited

U.S. PATENT DOCUMENTS

| 4,422,459 A | 12/1983 | Simson |
| 5,046,504 A | 9/1991 | Albert et al. |
| 5,117,833 A | 6/1992 | Albert et al. |
| 5,348,020 A | 9/1994 | Hutson |
| 5,404,877 A | 4/1995 | Nolan et al. |

(Continued)

FOREIGN PATENT DOCUMENTS

| WO | WO 2005/104937 | 11/2005 |
| WO | WO 2008/015683 | 2/2008 |

OTHER PUBLICATIONS

International Search Report and the Written Oponion Dated Jul. 18, 2008 From the International Searching Authority Re.: Application No. PCT/IL07/00971.

(Continued)

*Primary Examiner* — Catherine Voorhees

(57) ABSTRACT

Detecting cardiac ischemia by detecting local changes in high frequency ECG parameters. Local changes may be, for example, local reduction in RMS of high frequency components, for example, during a stress test.

18 Claims, 8 Drawing Sheets

(56) References Cited

U.S. PATENT DOCUMENTS

| | | | |
|---|---|---|---|
| 5,655,540 | A | 8/1997 | Seegobin et al. |
| 5,954,664 | A | 9/1999 | Seegobin |
| 6,128,526 | A | 10/2000 | Stadler et al. |
| 6,600,949 | B1 | 7/2003 | Turcott |
| 7,113,820 | B2 | 9/2006 | Schlegel et al. |
| 7,151,957 | B2 | 12/2006 | Beker et al. |
| 7,239,988 | B2 | 7/2007 | Hasson et al. |
| 7,386,340 | B2 | 6/2008 | Schlegel et al. |
| 7,412,283 | B2 | 8/2008 | Ginzburg et al. |
| 7,539,535 | B1 | 5/2009 | Schlegel et al. |
| 2003/0013978 | A1 | 1/2003 | Schlegel et al. |
| 2003/0208129 | A1 | 11/2003 | Beker et al. |
| 2004/0039292 | A1 | 2/2004 | Schlegel et al. |
| 2004/0215092 | A1* | 10/2004 | Fischell et al. ........... 600/515 |
| 2005/0101873 | A1* | 5/2005 | Misczynski et al. ........... 600/509 |
| 2005/0177049 | A1 | 8/2005 | Hardahl et al. |
| 2006/0074451 | A1 | 4/2006 | Chen et al. |
| 2006/0206033 | A1* | 9/2006 | Guerrero et al. ........... 600/523 |
| 2007/0066907 | A1 | 3/2007 | Beker et al. |
| 2008/0188762 | A1 | 8/2008 | John et al. |
| 2008/0194978 | A1 | 8/2008 | Beker et al. |
| 2009/0318820 | A1 | 12/2009 | Toledo et al. |
| 2010/0222688 | A1 | 9/2010 | Fischell et al. |
| 2011/0152661 | A1 | 6/2011 | Feldman et al. |

OTHER PUBLICATIONS

Communication Pursuant to Article 94(3) EPC Dated Jul. 11, 2012 From the European Patent Office Re. Application No. 07790026.4.
Communication Pursuant to Rules 70(2) and 70a(2) EPC Dated Oct. 24, 2011 From the European Patent Office Re. Application No. 07790026.4.
International Search Report and the Written Opinion Dated Jul. 18, 2008 From the International Searching Authority Re. Application No. PCT/IL07/00971.
Notice of Allowance Dated Jun. 12, 2013 From the US Patent and Trademark Office Re. U.S. Appl. No. 12/375,544.
Notice of Allowance Dated Sep. 13, 2013 From the US Patent and Trademark Office Re. U.S. Appl. No. 13/552,712.
Office Action Dated Apr. 14, 2010 From the State Intellectual Property Office of the People's Republic of China Re. Application No. 200780035563.2 and Its Translation Into English.
Official Action Dated Aug. 6, 2013 From the US Patent and Trademark Office Re. U.S. Appl. No. 13/552,712.
Official Action Dated Mar. 6, 2013 From the US Patent and Trademark Office Re. U.S. Appl. No. 12/375,544.
Official Action Dated Jun. 10, 2011 From the US Patent and Trademark Office Re. U.S. Appl. No. 12/375,544.
Official Action Dated Feb. 27, 2012 From the US Patent and Trademark Office Re. U.S. Appl. No. 12/375,544.
Response Dated Dec. 6, 2011 to Official Action of Jun. 10, 2011 From the US Patent and Trademark Office Re. U.S. Appl. No. 12/375,544.
Response Dated Aug. 19, 2010 to Office Action of Apr. 14, 2010 From the State Intellectual Property Office of the People's Republic of China Re. Application No. 200780035563.2.
Response Dated Dec. 19, 2011 to Office Action of Oct. 19, 2011 From the State Intellectual Property Office of the People's Republic of China Re. Application No. 200780035563.2.
Supplementary European Search Report and the European Search Opinion Dated Oct. 5, 2011 From the European Patent Office Re. Application No. 07790026.4.
Translation of Office Action Dated Jul. 3, 2012 From the State Intellectual Property Office of the People's Republic of China Re. Application No. 200780035563.2.
Translation of Office Action Dated Oct. 19, 2011 From the State Intellectual Property Office of the People's Republic of China Re. Application No. 200780035563.2.
Abboud et al. "Analysis of High-Frequency Mid-QRS Potentials Vs ST Segment and T Wave Analysis for the Diagnosis of Ischcmic Heart Disease", Computers in Cardiology, 30: 813-814, 2003.
Beker et al. "Analysis of High Frequency QRS Potential During Exercise Testing in Patients With Coronary Artery Disease and in Health Subjects", PACE, 19(Pt.I): 2040-2050, Dec. 1996.
Pettersson et al. "Changes in High-Frequency QRS Components Are More Sensitive Than ST-Segment Deviation for Detecting Acute Coronary Artery Occlusion", Journal of the American College of Cardiology, JACC, 36(6): 1827-1834, 2000.
Rahman et al. "High-Frequency QRS Electrocardiogram Predicts Perfusion Defects During Myocardial Perfusion Imaging", Journal of Electrocardiology, 39: 73-81, 2006.
Sharir et al. "Detection of Stress-Induced Myocardial Ischemia Using Analysis of Depolarization Abnormalities", JACC, Abstracts—Imaging and Diagnostic Testing, A297: #1054-264, Mar. 10, 2009.
Sharir et al. "Incremental Diagnostic Value of High-Frequency QRS Analysis for Identifying Stress-Induced Ischemia", JACC, Exercise Testing: Modern Diagnostic and Prognostic Markers, Abstracts—Diagnostic Testing, 132A: #828-3, Mar. 13, 2006.
International Search Report and the Written Oponion Dated Oct. 21, 2013 From the International Searching Authority Re.: Application No. PCT/IL2013/050502.

* cited by examiner

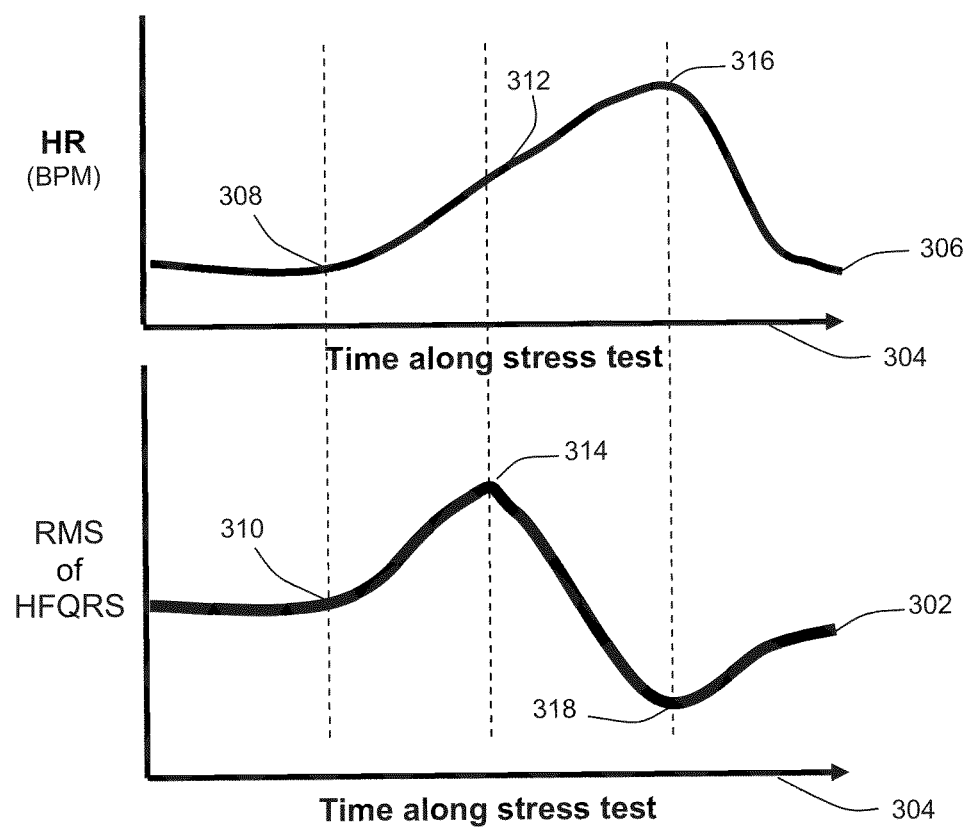

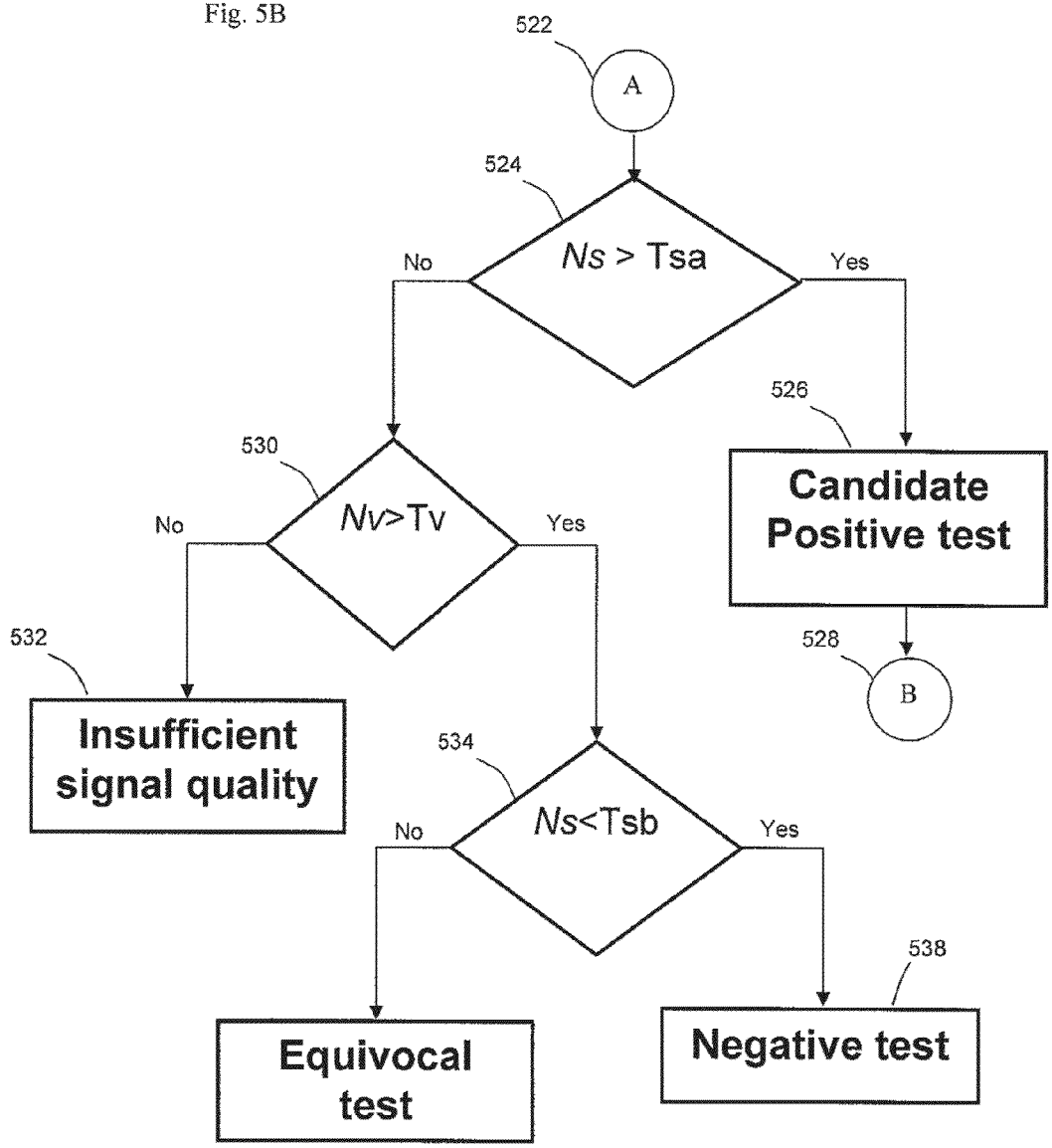

Fig. 7A
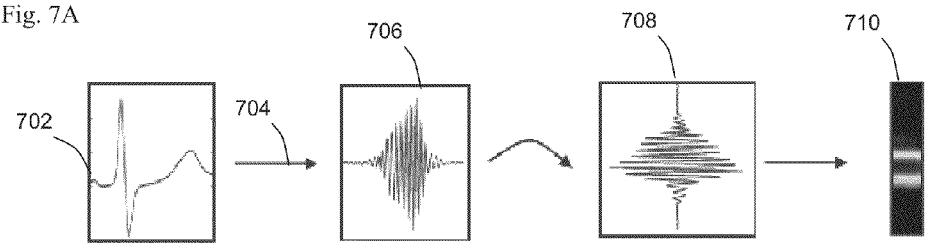
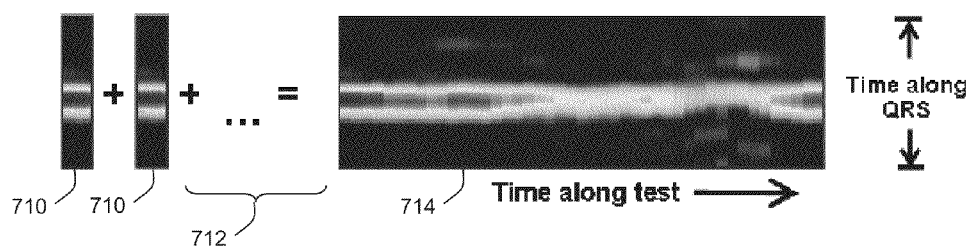
Fig. 7B
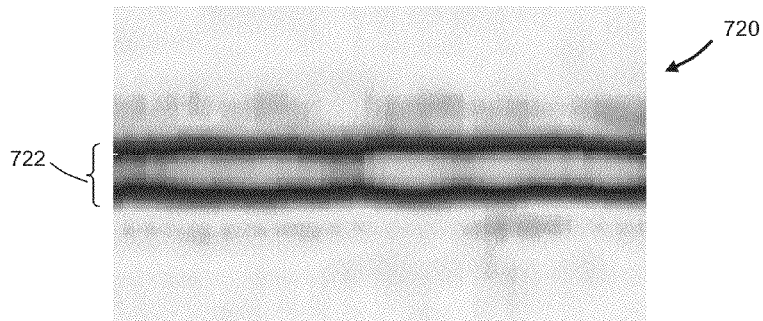
Fig. 7C
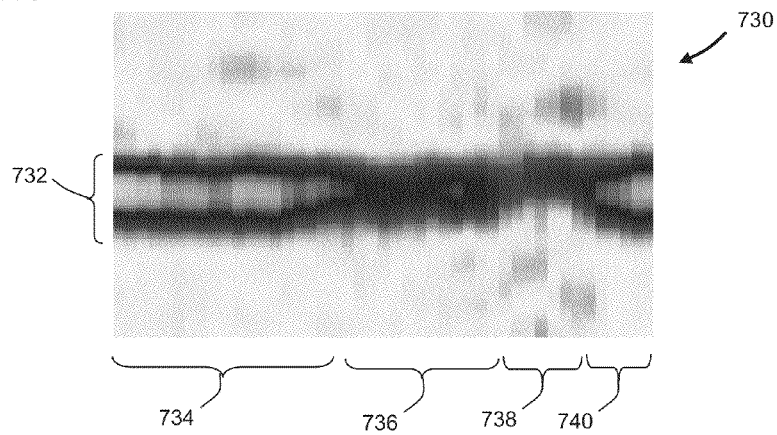

APPARATUS AND METHOD FOR IDENTIFYING MYOCARDIAL ISCHEMIA USING ANALYSIS OF HIGH FREQUENCY QRS POTENTIALS

RELATED APPLICATIONS

This application is a continuation of U.S. patent application Ser. No. 12/375,544, filed on Jan. 29, 2009, which is a National Phase of PCT Patent Application No. PCT/IL2007/000971 having International filing date of Aug. 2, 2007, which claims the benefit of priorities under 35 U.S.C. 119(e) of U.S. Provisional Patent Application No. 60/821,268, filed on Aug. 3, 2006. The contents of the above Applications are all incorporated herein by reference.

FIELD OF THE INVENTION

The invention relates to an analysis of ECG signals. Some embodiments relate diagnostics characteristics of high frequency components of a QRS complex.

BACKGROUND

Myocardial ischemia is often detected by the application of cardiac stress, for example, stress caused by exercise or pharmaceutical injection. In general, ischemia conditions can be detected by changes in the ECG signals or by techniques of cardiac imaging.

One type of ECG analysis includes analyzing high frequency components in a QRS complex of a heart beat. One of the indications for ischemia is a reduction in the intensity of a high frequency band in the QRS complex. For example, Beker et al ("Analysis of High Frequency QRS Potential during Exercise Testing Patients with Coronary Artery Disease and in Healthy Subjects", Biomedical Engineering Department, Faculty of Engineering, Tel-Aviv University, 1995), Abboud et al (Analysis of High Frequency Mid-QRS Potentials vs ST segment and T Wave Analysis for the Diagnosis of Ischemic Heart Disease, IEEE Computers in Cardiology 2003; 30:813-814), Sharir et al (Detection of Stress-Induced Myocardial Ischemia using Analysis of High-Frequency QRS Components. Journal of the American College of Cardiology 2006: 47 (4), 132A), the disclosures of which are hereby incorporated herein by reference, discuss analyzing a high frequency signal of the QRS complex during an exercise test.

US patent applications 20030013978 by Schlegel et al. and 20040039292 by Schlegel et al. and Rahman et al (High-frequency QRS electrocardiogram predicts perfusion defects during myocardial perfusion imaging, Journal of Electrocardiology 2006:39; 73-81) disclose RAZ analysis of the high frequency waveform.

U.S. Pat. No. 7,151,957 to Beker et al., the contents of which are hereby incorporated by reference, discloses methods of high frequency waveform averaging to obtain an improved signal to noise ratio from such a signal.

Simpson, in U.S. Pat. No. 4,422,459, teaches a system which analyzes only the late portion of the QRS interval and early portion of the ST segment, and in an off-line fashion. Albert et al., U.S. Pat. No. 5,117,833, partially focuses on analyzing signals within the mid-portion of the QRS interval for the indication of cardiac abnormality. Albert et al., U.S. Pat. No. 5,046,504, similarly teaches the acquisition of QRS data and subsequent analysis. Seegobin, in U.S. Pat. Nos. 5,655,540 and 5,954,664, provides a method for identifying coronary artery disease. Hutson, U.S. Pat. No. 5,348,020, teaches a technique of near real-time analysis and display. Beker, in patent application WO2005/104937, teaches a technique for analysis of high frequency QRS complexes. Pettersson et al (Changes in high-frequency QRS components are more sensitive than ST-segment deviation for detecting acute coronary artery occlusion. Journal of the American College of Cardiology 2000; 36:1827-34) analyzed changes in HF-QRS in patients undergoing coronary angioplasty.

U.S. Pat. No. 7,113,820 to Schlegel et al., the disclosure of which is incorporated by reference, shows a detection of a reduced amplitude zone (RAZ) within the high frequency waveform of ECG signals.

SUMMARY OF THE INVENTION

An aspect of some exemplary embodiments of the invention relates to ischemia and/or infarction detection using a high frequency ECG signal, by detecting a relative reduction in amplitude, or other local change optionally during a stress condition. In an exemplary embodiment of the invention, the detected reduction is relative to a maximum amplitude detected during the stress condition. Optionally or alternatively, the detection includes determining both relative and absolute reduction. In an exemplary embodiment of the invention, a local change indicates an instant change in the functioning of the underlying cardiac tissue, as compared to a comparison to a baseline which cannot show such an instant change for time-varying parameters. Optionally, the change is compared to an expected value. In some cases, the change is exhibited as a non-change or as a small increase, when a larger increase would be expected for that patient.

In exemplary embodiments of the invention, the decrease is evaluated at a cardiac stress relative to a rest state in an exercise. Optionally, the cardiac stress is at the peak of exercise such as in a standard stress test (e.g. ACC/AHA Exercise Testing Guidelines), while the rest state is before or after the beginning of the exercise. Optionally or alternatively, the decrease is relative to a preset value. Optionally, the comparison is to a peak value, rather than or in addition to comparison to a peak stress condition.

In exemplary embodiments of the invention, the diagnosis is based on the amount of decrease. Optionally, the diagnosis is based on one or more threshold values. Optionally, the threshold value is defined as a percentage of and/or a change relative to a rest condition and/or preset value and/or maximal value.

In exemplary embodiments of the invention, the decrease is evaluated during a single exercise. Optionally, the decrease is determined between two or more exercises.

In exemplary embodiments of the invention, the intensity of the high frequency component is determined as the peak intensity. Optionally, the intensity is determined as an arithmetic and/or statistical measure (e.g. average or root mean square) of the high frequency waveform.

In exemplary embodiments of the invention, the high frequency is above 100 Hz. Optionally, the high frequency is about a range between 150 Hz and 250 Hz.

In exemplary embodiments of the invention, the ECG signal is sampled from a plurality of leads. Optionally, the reduction is determined as a combination of the reduction of the respective signals of one or more leads. Optionally, signals with high noise (e.g. low signal to noise ratio) are discarded from the evaluation.

In exemplary embodiments of the invention, the ischemia diagnosis may be combined with other techniques, for example, ECG waveform analysis or the Duke Treadmill Score (DTS). Optionally, particular types and/or causes of ischemia and infarction are diagnosed by the combination of results from several techniques.

In exemplary embodiments of the invention, diagnosis results in one or more treatments. In an exemplary embodiment of the invention, a medication, such as beta-blockers or lipid-lowering medications, optionally at one or more dosage levels, are administered following ischemia diagnosis according to the invention. Optionally, medications are administered according to a combination of results from several techniques.

In accordance with one aspect of the present invention there is provided an apparatus for the quantification of features in the QRST waveform, comprising:

an ECG input unit for receiving at least one conventional PQRST complex from at least one ECG lead;

an HF-QRS input unit, for receiving at least one high frequency (HF) QRS complex from at least one ECG lead, refers herein to the range above 100 Hz, preferably to the range of 100 Hz-500 Hz, and more preferably to the range of 150 Hz-250 Hz of the signal;

a primary HF analyzer, associated with the HF-QRS input unit, for calculating a vector of primary HF indices from the at least one high frequency (HF) QRS complex, and a secondary HF analyzer, connected to the HF-QRS input unit and associated with the primary HF analyzer, for deriving a vector of secondary HF indices, and a primary ECG analyzer connected to the ECG input unit, for calculating a vector of ECG indices from at least one QRST complex, and a secondary ECG analyzer, connected to the ECG input unit and associated to primary ECG analyzer, for deriving a vector of secondary ECG indices, and preferably a decision algorithm comprising a set of rules involving at least one of following: the vector of primary indices, the vector of secondary HF indices, the vector of primary ECG indices and the vector of secondary ECG indices.

Preferably, the components of the vector of primary HF indices are constructed using statistical functions of at least one QRS complex.

Preferably, the components of the vector of primary HF indices are dependent of each other.

Alternately, the components of the vector of primary HF indices are independent of each other.

Preferably, the components of the vector of secondary HF indices are dependent of each other.

Alternately, the components of the vector of secondary HF indices are independent of each other.

Preferably, the components of the vector of primary ECG indices are dependent of each other.

Alternately, the components of the vector of primary ECG indices are independent of each other.

Preferably, the components of the vector of secondary ECG indices are dependent of each other.

Alternately, the components of the vector of secondary ECG indices are independent of each other.

Preferably, the components of the vector of primary HF indices include at least one of a group comprising:
an RMS level of at least one HF QRS complex,
a standard deviation within an HF QRS complex,
a standard deviation over a plurality of HF QRS complexes,
a kurtosis within an HF QRS complex,
a kurtosis over a plurality of HF QRS complexes,
a central moment of any order within an HF QRS complex,
a central moment of any order over a plurality of HF QRS complexes,
an entropy level within an HF QRS complex,
an entropy level over a plurality of HF QRS complexes,
an RMS level of the noise of at least one HF QRS complex,
a signal-to-noise ratio of at least one HF QRS complex,
a cross-correlation value of the HF QRS complex with a template waveform,
and
derivations of any one thereof.

Preferably, the components of the vector of primary HF indices include at least one of a group comprising:
a function of an envelope of an HF QRS complex,
a function over a plurality of envelopes of HF QRS complexes,
a kurtosis within an envelope of an HF QRS complex,
a kurtosis over a plurality of envelopes of HF QRS complexes,
a central moment of any order within an envelope of an HF QRS complex,
a central moment of any order over a plurality of envelopes of HF QRS complexes,
an entropy level within an envelope of an HF QRS complex,
an entropy level over a plurality of envelopes of HF QRS complexes,
an envelope maximum over an HF QRS complex,
an envelope maximum over a plurality of HF QRS complexes,
an envelope width of an HF QRS complex,
an envelope width over a plurality of HF QRS complexes,
a cross-correlation value of said envelope of HF QRS complex with a template
and
derivations of any one thereof.

Preferably, the components of the vector of primary HF indices are running averages of these indices.

Preferably, a component of the vector of secondary HF indices is a running average of a component of the vector of primary HF indices.

Preferably, components of the vector of secondary HF indices are functions of:

(a) components of the first vector of primary HF indices calculated by the primary HF analyzer from a first high frequency (HF) range QRS complex received at a first time period and (b) components of a second vector of primary HF indices calculated by the primary HF analyzer from a second high frequency (HF) range QRS complex received at a second time period.

Preferably, components of the vector of primary ECG indices include at least one of a group comprising of any known feature of the ECG or any known electrocardiographic manifestation of cardiac disease. By way of example, components of the vector of primary ECG indices may include at least of the following:
QRS duration of at least one QRS complex,
ST segment level of at least one QRST complex,
Presence of upsloping ST segment in at least one QRS complex,
Presence of downsloping ST segment in at least one QRS complex,
Presence of horizontal ST segment in at least one QRS complex,
QT interval in at least one QRS complex,
QTc interval in at least one QRS complex,
PR interval in at least one QRS complex,
Electrical axis in at least one QRS complex,
Heart rate,
T-wave inversion in at least one QRS complex, T-wave peakedness in at least one QRS complex,
T-wave abnormality in at least one QRS complex,
Presence of atrial arrhythmias,
Presence of ventricular arrhythmias,
Presence of incomplete left bundle branch block,
Presence of incomplete right bundle branch block,
Presence of complete left bundle branch block,
Presence of complete right bundle branch block,
Presence of conduction blocks,
Presence of P-wave abnormalities in at least one QRS complex,
Presence of slurs or notches in at least one QRS complex,
Presence of conduction abnormalities,
Amplitude of at least one QRS complex, and
Wolff-Parkinson-White syndrome.

Preferably, a component of the vector of secondary ECG indices is a running average of a component of the vector of primary ECG indices.

Preferably, components of the vector of secondary ECG indices are functions of:

(a) components of the first vector of primary ECG indices calculated by the primary ECG indices analyzer from a the ECG received at a first time period and (b) components of a second vector of primary ECG indices calculated by the primary ECG indices analyzer from the ECG received at a second time period.

Preferably, the decision algorithm includes a set of rules that involve a linear combination of the components of the vector of primary indices, components of the vector of secondary HF indices, components of the vector of primary ECG indices and components of the vector of secondary ECG indices Alternately, the decision algorithm includes a set of rules that involve a nonlinear combination of the components of the vector of primary indices, components of the vector of secondary HF indices, components of the vector of primary ECG indices and components of the vector of secondary ECG indices.

Preferably, the decision algorithm is based on a decision tree that involves the components of the vector of primary indices, components of the vector of secondary HF indices, components of the vector of primary ECG indices and components of the vector of secondary ECG indices.

Preferably, the decision algorithm is based on a neural network that involves the components of the vector of primary indices, components of the vector of secondary HF indices, components of the vector of primary ECG indices and components of the vector of secondary ECG indices.

Preferably, the decision algorithm is operable to indicate at least one of the presence and/or severity of an ischemic event or an ischemic heart condition or ischemic heart disease.

Preferably, at least one of the primary HF analyzer and the secondary HF analyzer and the primary ECG analyzer and the secondary ECG analyzer is configured to commence the calculating or the deriving respectively while the input unit continues to receive data, thereby providing an on-line quantification.

The apparatus may comprise a reduction unit associated with the primary HF analyzer and/or the secondary HF analyzer, for excluding outermost points per predetermined unit time intervals.

The apparatus may comprise a reduction unit associated with the primary ECG analyzer and/or the secondary ECG analyzer for excluding outermost points per predetermined unit time intervals.

The apparatus is preferably further configured to issue an alarm signal upon detection of an indication of ischemia.

There is thus provided in accordance with an exemplary embodiment of the invention, a method for analyzing ECG signals, comprising:

(a) providing at least one ECG signal recorded from a body;

(b) determining the value of at least one parameter of a high frequency band of said ECG signal; and (c) generating an alert responsive to a local change of the parameter value during a test.

Optionally, said alert comprises diagnosing ischemia.

Optionally or alternatively, said parameter is an amplitude related parameter.

Optionally, said local change is a change compared to a value under similar conditions at a different time.

Optionally, said local change is a change compared to the signal at a short time before.

Optionally, said test comprises a stress test. Optionally, said local change is a change relative to a maximum stress condition. Optionally or alternatively, said local change is a change relative to a maximum signal condition.

In an exemplary embodiment of the invention, said test comprises a monitoring event.

In an exemplary embodiment of the invention, said test comprises a treatment event.

In an exemplary embodiment of the invention, said test comprises a monitoring of at least 1 hour.

In an exemplary embodiment of the invention, said test comprises a monitoring of at least 2 hours.

In an exemplary embodiment of the invention, generating an alert comprises performing an additional test.

In an exemplary embodiment of the invention, generating an alert comprises generating an alert responsive to at least one additional physiological considerations. Optionally, said at least one additional physiological consideration comprises a low-frequency ECG.

In an exemplary embodiment of the invention, said at least one additional physiological consideration comprises an absolute change in a high frequency parameter.

In an exemplary embodiment of the invention, the ECG signal is sampled from a plurality of leads. Optionally, a lead with a high level of noise is discarded from the diagnosis. Optionally, an ischemia diagnosis depends on the analysis results of multiple leads. Optionally, a lead value is weighted according to its noise level.

There is also provided in accordance with an exemplary embodiment of the invention, a method of detecting an ischemic event, comprising:

(a) analyzing a high frequency band of an ECG signal collected from a plurality of heartbeats to detect a change in at least one parameter;

(b) identifying the change as being indicative of a potential ischemic event;

(c) further analyzing data associated with said potential event to increase a reliability of said identifying. Optionally, said analyzing comprises analyzing after a stress test starts. Optionally or alternatively, said analyzing comprises analyzing during a non-stress situation. Optionally or alternatively, said analyzing comprises identifying a transient stress event based on a change in heart rate. Optionally or alternatively, said further analyzing comprises analyzing said ECG signal. Optionally, said further analyzing comprises analyzing said a high frequency band of said ECG signal.

In an exemplary embodiment of the invention, said further analyzing comprises analyzing additional data.

In an exemplary embodiment of the invention, said analyzing comprises scanning a stream of ECG data for said change.

In an exemplary embodiment of the invention, said analyzing comprises predetermining one or more points in time to analyze for said change.

In an exemplary embodiment of the invention, said identifying comprises identifying a change indicative of a reduction in conduction velocity.

In an exemplary embodiment of the invention, said identifying comprises identifying a change indicative of an increase in conduction velocity.

There is also provide din accordance with an exemplary embodiment of the invention, a method of detecting an ischemic event, comprising:

(a) scanning a high frequency band of an ECG signal collected from a plurality of heartbeats to detect a change in at least one parameter, at a point in time not pre-specified; and (b) identifying the change as being indicative of a potential ischemic event.

Optionally, said change comprises a local change.

Optionally or alternatively, said change comprises a reduction in HF amplitude.

In an exemplary embodiment of the invention, the method comprises further analyzing data associated with said potential event to increase a reliability of said identifying.

Optionally, said scanning comprises scanning in a monitoring setting.

Optionally or alternatively, said scanning comprises scanning in a stress-testing setting.

There is also provided in accordance with an exemplary embodiment of the invention, apparatus for ECG signal analysis, comprising:

(a) an input for an ECG signal;
(b) a high-frequency band extractor which extracts a HF band from said signal;
(c) a filter configured to analyze said HF band and detect a local change; and
(d) an output which generates an output signal responsive to a detected change.

Optionally, the apparatus includes a processor configured to analyze low frequency components of said ECG signal.

Optionally, the apparatus is mounted as a wearable ECG monitor.

Optionally, the apparatus is configured as a part of an implantable device.

Optionally, the apparatus is configured as a part of an exercise stress test system.

Optionally, said filter analyses said HF band using a cross-correlation method to detect said local change. Optionally or alternatively, said filter analyses said HF band to determine a change in a kurtosis parameter. Optionally or alternatively, the apparatus comprises a memory adapted to store a reference value from a different session.

BRIEF DESCRIPTION OF THE DRAWINGS

Non-limiting examples of embodiments of the present invention are described with reference to figures listed below. Identical or equivalent structures, elements or parts that appear in some figures are labeled with the same numerals.

FIG. 3 schematically illustrates an intensity reduction of a quantification of high frequency QRS HFQRS with respect to a duration of a stress exercise and with respect to heart rate in an ischemic subject, in accordance with an exemplary embodiment of the invention;

FIG. 5B is a continuation of the flowchart of FIG. 5A or illustrates an alternative flowchart for determining the significance of intensity reduction of a plurality of leads, in accordance with an exemplary embodiment of the invention.

FIG. 7A schematically illustrates a HyperMap and a HyperMap derivation, in accordance with an exemplary embodiment of the invention;

FIG. 7B schematically illustrates a HyperMap of a normal patient in the course of a test, in accordance with an exemplary embodiment of the invention; and FIG. 7C schematically illustrates a HyperMap of an ischemic patient in the course of a test, in accordance with an exemplary embodiment of the invention.

DETAILED DESCRIPTION OF EMBODIMENTS OF THE INVENTION

The non-limiting headings that follow are intended for clarity only.

Framework

In exemplary embodiments of the invention, a high frequency ECG signal is used, optionally with other features of the ECG signal, to diagnose ischemia in a patient. Optionally, the ECG-based detection is combined with other methods or procedures to evaluate risk of disease and/or to determine a treatment.

Figure 1:
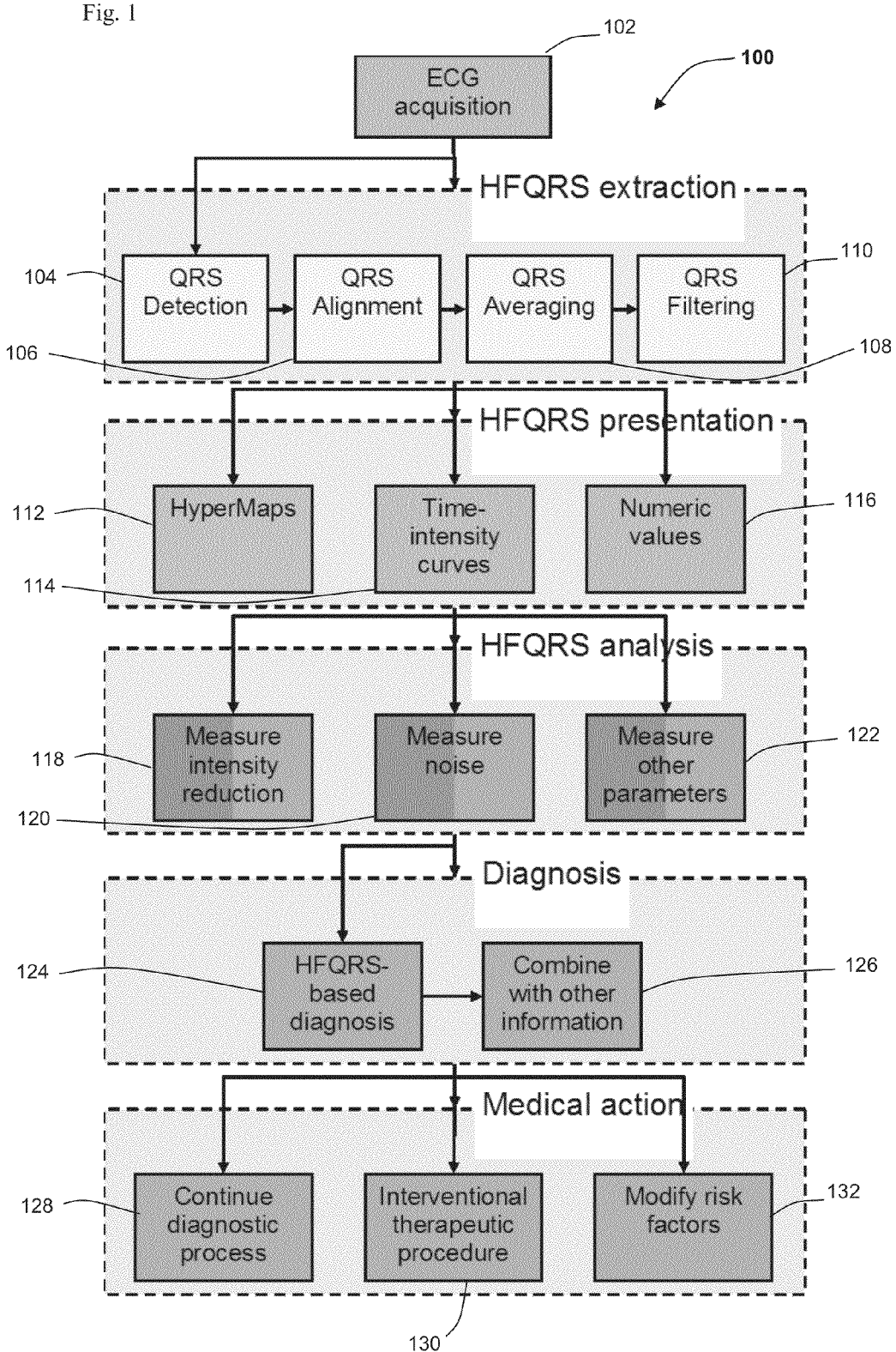
FIG. 1 illustrates a flowchart depicting a framework of operations, in accordance with an exemplary embodiment of the invention.

FIG. 1 illustrates a flowchart 100 depicting a framework of operations, in accordance with an exemplary embodiment of the invention. The operations will be reviewed here briefly, and particular ones will be further discussed later on. Exemplary methods of carrying out some of the operations with lighter shade were described in other applications, as follows:

Operations 106 and 108 were described in Published Us Patent Application No. 2008/0194978 of Beker et al, entitled "Apparatus And Method For Analysis Of High Frequency QRS Complexes";

Operation 112 was described in "Apparatus And Method For Efficient Representation Of Periodic And Nearly Periodic Signals For Analysis", U.S. Pat. No. 7,239,988

Operations 118, 120 and 122 were partly described in "Apparatus And Method For Efficient Representation Of Periodic And Nearly Periodic Signals For Analysis", U.S. Pat. No. 7,239,988 to Hasson et al; and additional possibly useful operations may be described in, for example, US published patent application No. 2007-0066907 of Beker et al, and U.S. Pat. No. 7,151,957 to Beker et al, the disclosures of all of which are incorporated herein by reference.

In exemplary embodiments of the invention, ECG signals are acquired from one or more leads (102). The sampled signals are analyzed to extract the QRS-complex waveform (104), for example, by correlation with a template and/or previous QRS waveforms, and/or previous averaged QRS waveforms.

In exemplary embodiments of the invention, the QRS-complex waveform (hereinafter QRS) are aligned (106) and averaged (108) to obtain a representative QRS, at least for a certain period.

In exemplary embodiments of the invention, the representative QRS is filtered (110) to obtain high frequency contents of the QRS waveform, that is, a representative high frequency QRS (hereinafter HFQRS).

In exemplary embodiments of the invention, the HFQRS, and optionally the QRS, is color coded (112), and optionally charted (114), for visual evaluation. Also, numerical representation of the HFQRS, and optionally QRS, is obtained for further processing (116).

In exemplary embodiments of the invention, the HFQRS are analyzed to extract one or more quantifications of the HFQRS waveform, for example, maximal amplitude. The quantification is used to evaluate the quantification magnitude relative to that of another HFQRS from another period and/or another reference (118). Optionally, the quantification magnitude is evaluated under physical and/or physiological stress relative to a relaxed, or lower stress, condition.

Particularly, without limiting, the evaluation comprises evaluating the reduction of the quantification in a stress condition to that of a lower stress condition (intensity reduction) in order to obtain an ischemia diagnosis (124).

In exemplary embodiments of the invention, operations 112, 114 and 116 may be performed sequentially, or, at least partially, in parallel.

In exemplary embodiments of the invention, either sequentially or in parallel to intensity reduction 118, the signals noise, and optionally the noise of the QRS or HFQRS, is evaluated to determine the quality of the signals and, optionally to filter and/or reject noisy signals (120).

In exemplary embodiments of the invention, either sequentially to, or parallel with 118 or 120, other parameters are derived from the QRS or HFQRS (122). For example, entropy of a HFQRS waveform or a kurtosis within a HFQRS waveform. The additional parameters may be used to improve (126) a subsequent diagnosis (124).

In exemplary embodiments of the invention, according to the diagnosis, the patient is either referred for further tests and/or diagnosis (128), and/or a therapeutic treatment is determined (130), and/or medical treatment is offered to modify the patient's risks for disease (132).

ECG Acquisition

In exemplary embodiments of the invention, ECG signal is obtained from one or more leads. Optionally, up to 12 leads (and optionally 10) or more are used to obtain up to 12 or more respective signals.

In exemplary embodiments of the invention, the signals are obtained with equipment that preserves the high frequency contents of the signals. Optionally, the high frequency is over 100 Hz and optionally up to about 500 Hz.

In exemplary embodiments of the invention, the acquired signals, possibly amplified (e.g. by a standard ECG unit), are sampled by a computer. Optionally the sampling is aided by other equipment, such as an A/D converter. Optionally, the signals are analyzed to reject noisy signals. Optionally, the signals are preprocessed such as by low-pass filter (or equivalent, such as averaging) so that subsequent operations and derivations are sufficiently stable and reliable. Optionally, the preprocessing is performed on a copy of the acquired signals, so that high frequency contents are preserved in another copy.

In exemplary embodiments of the invention, unless otherwise specified, subsequent operations are performed on the signal of each lead separately, or on signals that are composite or calculated form multiple leads. In some embodiments, specific leads, for example, local leads or catheter-based leads are used. The ECG signals may also be acquired using other means, such as magnetic field measurement.

Representative QRS

A typical ECG signal comprise of a train of waves (P-QRS-T-u). The diagnosis is based, at least partially, on properties of the QRS waveform. Particularly, without limiting, the diagnosis is based on a combination of several QRS waveforms, optionally consecutive, or interspersed, within a certain time period (window). Therefore, the QRS waveforms have to be detected and aligned to enable their analysis and/or combination.

In exemplary embodiments of the invention the period is uniform, for example, 10 seconds. Optionally, the period is according to the duration of the test. Optionally, the period is responsive to factors such as heart rate, heart rate change, or other factors such as signal noise or signal to noise ratio.

In exemplary embodiments of the invention, the detection of the QRS is performed with a correlation to a reference QRS-complex waveform (e.g., using a template). Optionally, the reference is a previous QRS, or a combination of previous QRS. Optionally, the reference is an average (or other statistics) of previous QRS. Optionally, the reference is obtained from the patient at the beginning of a diagnosis test or at a different time, optionally, with other equipment. Optionally or alternatively, a preset template is used, optionally adapted to the length and/or amplitude of the patient QRS.

In exemplary embodiments of the invention, when a QRS waveform does not match the template (i.e. low correlation) the QRS is rejected from further processing. Optionally, a threshold correlation value is used for accepting a QRS.

In exemplary embodiments of the invention, in order to combine the detected QRS waveforms, the QRS are aligned so that that their waveforms coincide within an acceptable range. Optionally, the alignment is performed by a correlation procedure to obtain a sufficient correlation value (match) with a reference. Optionally, the reference is a preceding QRS or a combination of preceding QRS. Optionally, the reference is a template as described above.

In exemplary embodiments of the invention, the aligned QRS are combined. Optionally, the combination is an average of the QRS waveforms. Optionally, other statistics such a band around the mean, or RMS, or median is used, optionally ignoring samples with a large deviation from the mean value.

In exemplary embodiments of the invention, the combined QRS waveforms comprises a representative QRS for the time period. Optionally, the time period is the period from which the QRS waveforms were selected. Optionally, the period is larger, or extends beyond, the time from which the QRS were selected (e.g. the QRS were selected from the center of the time period).

QRS Filtering

In exemplary embodiments of the invention, the representative QRS is filtered to extract the high frequency component (HF). Optionally, the extraction is performed using a high-pass and/or band-pass filter. Optionally, the high frequency is over 100 Hz. Optionally, the high frequency is between about 100 Hz and about 500 Hz. Preferably, without limiting, the high frequency is between about 150 Hz and about 250 Hz. The high frequency component of the representative QRS is a representative high frequency QRS (HFQRS) for the respective period.

In an alternative exemplary embodiment of the invention, the HFQRS is obtained by filtering the ECG signal and performing the identification, alignment and combination on the high frequency ECG signal as described above. Optionally, the identification, alignment and combination operations are performed on the filtered signals in coordination with the those of the ECG signal, because the ECG waveform is typically simpler and consistent over a time and thus more suitable for such operations.

Noise Reduction/Elimination

In exemplary embodiments of the invention, if the HFQRS waveform comprises a significant amount of noise then the signals of the respective lead are discarded from further processing. Optionally, the lead signals are discarded only if a minimal number or percentage of HFQRS waveforms comprise significant amount of noise. Optionally, a significant amount of noise comprises a signal to noise ratio below a certain threshold (Tn). Optionally, the number of leads rejected depends on the relative noise levels. For example, a minimum number of leads may be maintained. Optionally, noisier leads are weighted lower when making a decision.

In exemplary embodiments of the invention, the threshold Tn is 3. Optionally, the threshold is 2. Optionally, the threshold is 4. Optionally, the threshold is a value larger than 1 and lower than 10. Optionally, other noise determination methods are used, such as maximal amplitude of the noise (e.g. within a period), or average or other statistics of the noise amplitudes.

In alternative exemplary embodiments of the invention, noise is reduced to an acceptable level, e.g. below a certain level as described above, and the signals of the respective lead are not discarded. Optionally, the noise is reduced by a low-pass or band-pass filter or equivalents. Optionally, the noise is reduced provided that the waveforms of the HFQRS, or essential features thereof, are not affected to distort further evaluations and/or the diagnosis.

Intensity Reduction

In exemplary embodiments of the invention, unless otherwise specified and without limiting, the discussion below relates to a stress-induced ischemia that develops during exercise.

Figure 2A:
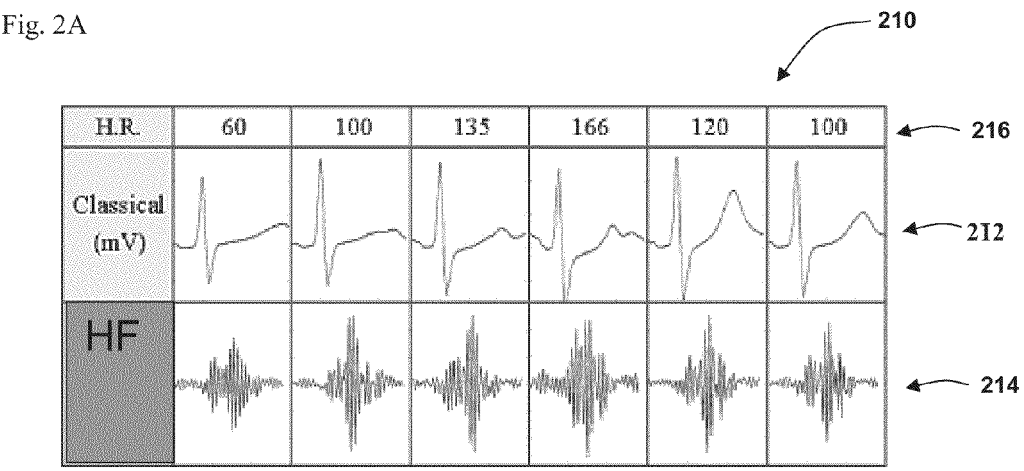
FIG. 2A illustrates samples of ECG and respective high frequency samples at different stages and different heart rates during a stress test of a healthy subject, in accordance with an exemplary embodiment of the invention.

FIG. 2A illustrates samples 210 of ECG 212 and respective high frequency samples 214 at different stages and different heart rates 216 during a stress test of a healthy subject. The morphology and intensities of the high frequency waveforms 214 are similar for all the stages above 60 beats per minute (about normal rate).

Figure 2B:
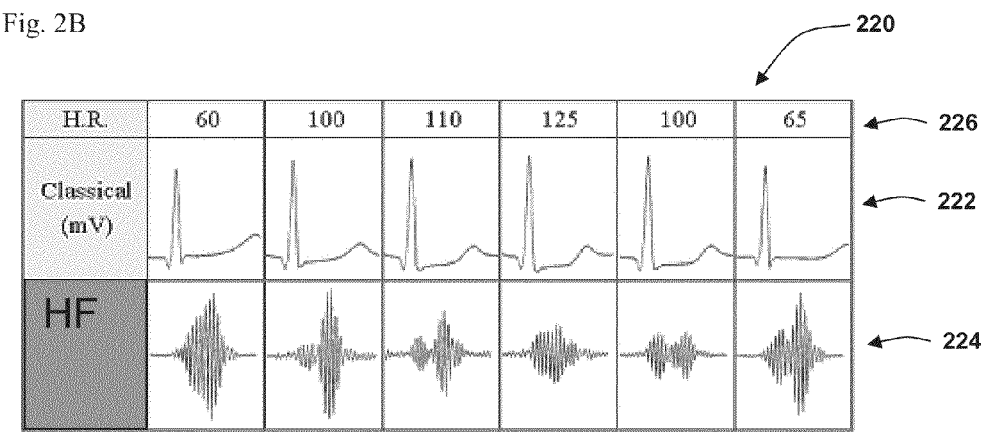
FIG. 2B illustrates samples of ECG and respective high frequency samples at different stages and different heart rates during a stress test of an ischemic subject, in accordance with an exemplary embodiment of the invention.

On the other hand, FIG. 2B illustrates samples 220 of ECG 222 and respective high frequency samples 224 at different stages and different heart rates 226 during a stress test of an ischemic subject. The morphology and intensities of the high frequency waveforms 224 vary as the stress (i.e. heart rate) varies, and the intensity decreases as the test progresses, and is restored to about its initial rest level (at 60 bpm) as the subject relaxes (65 bpm).

In exemplary embodiments of the invention, the duration of a stress exercise is divided to stages. A stage time period may be uniform, for example 10 seconds. Optionally the stages times are responsive to heart rate or the signal noise. For each stage a representative high frequency QRS (HFQRS) is derived as described above, and a quantification of the HFQRS is derived (hereinafter qHF).

In exemplary embodiments of the invention, a quantification of the HFQRS, qHF, is the maximal intensity amplitude of the HFQRS. Optionally, the quantification is the minimal amplitude. Optionally, the quantification is a statistics of the HFQRS such as average, RMS (Root Mean Square), or a standard deviation. Optionally or alternatively, the quantification is derived from the morphology of the HFQRS waveform, such as kurtosis or a value of a valley between peaks (Reduced Amplitude Zone, RAZ).

In exemplary embodiments of the invention, qHF is evaluated with respect to the time scale of the exercise and/or the respective heart rate. It was found that ischemic subjects exhibit a marked decrease of qHF as the exercise progresses and/or the heart rate increases, possibly after an initial increase.

FIG. 3 schematically illustrates an intensity reduction of a quantification qHF as RMS 302 with respect to a duration of a stress exercise 304, and with respect to heart rate 306, in an ischemic subject. As heart rate 306 begins to increase (308), so does qHF 302 (310). However, as heart rate 306 further increases (312), qHF 302 begins to decrease after reaching a peak (314). Furthermore, as heart rate 306 reaches a peak 316 with a subsequent relaxation, qHF 302 reaches a trough 318, with a subsequent increase. Therefore, a subject exhibiting intensity reduction similar to that of FIG. 3 can be diagnosed, or judged, as having ischemia, or at least a stressed-induced ischemia.

Intensity Reduction Evaluation

In exemplary embodiments of the invention, the qHF values from the stages of an exercise are collected and the maximal and minimal values, H and L respectively, are determined, provided that H precedes L. For example, 314 (H) and 318 (L) in FIG. 3.

In exemplary embodiments of the invention, in order to determine a significant intensity reduction, an absolute difference (Da) and a relative difference (Dr) between H and L have to exceed a respective threshold (Ta and Tr, respectively). Optionally, either one of an absolute difference or a relative difference between H and L is used, optionally with different thresholds than the combination of absolute and relative differences.

In exemplary embodiments of the invention, the absolute difference is expressed in voltage units. Optionally, other units are used, such as power.

In exemplary embodiments of the invention, the relative difference is with respect to H. Optionally, other relative expressions may be used, such as difference with respect to L, or with respect to an average of H and L, or other measures such as with respect to a qHF at a relaxed condition (e.g. rest).

In exemplary embodiments of the invention, the threshold for absolute difference (Ta) for qHF as RMS is 1 $\mu V$. Optionally, the threshold is lower than 1 $\mu V$ such as 0.5 $\mu V$ or 0.7 $\mu V$. Optionally, the threshold is larger than 1 $\mu V$, such as 1.5 $\mu V$ or 2 $\mu V$. Optionally, the threshold is set responsive to the calibration of the ECG input and/or sampling equipment. Optionally, Ta is different for different quantifications qHF.

In exemplary embodiments of the invention, the relative difference is defined as (H-L)/H and threshold for the relative difference (Tr) for qHF as RMS is 45%. Optionally, the threshold is lower than 45%, such as 30% or 40%. Optionally, the threshold is higher than 45%, such as 50% or 60% or 75% or 100%.

Figure 4:
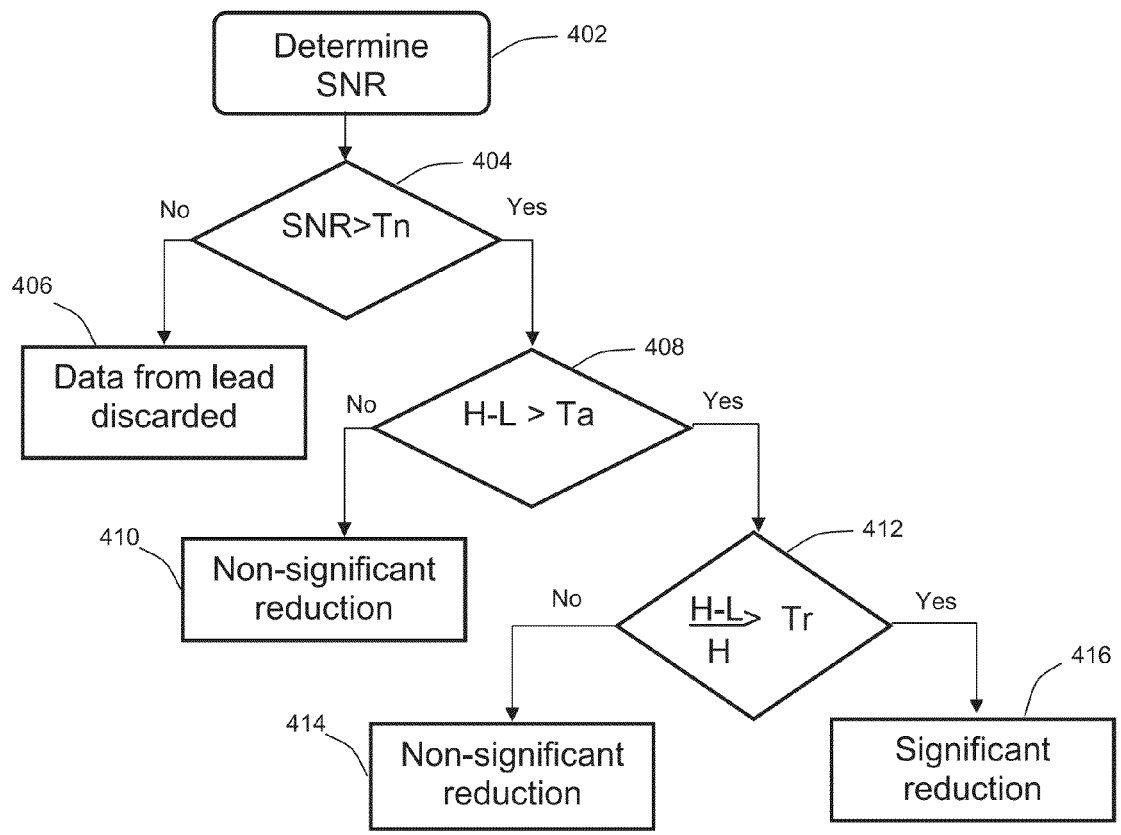
FIG. 4 illustrates a flowchart for determining a significant intensity reduction, in accordance with an exemplary embodiment of the invention.

FIG. 4 illustrates a flowchart for determining a significant intensity reduction, in accordance with an exemplary embodiment of the invention. To begin with, the noise level of the ECG signal and/or that of the one or more of the HFQRS is determined (402). If the signal to noise ratio (SNR) is larger than the threshold Tn (402), the respective lead is discarded from further operations (406).

In exemplary embodiments of the invention, provided that the noise level is acceptable, the absolute difference (H-L) is checked whether it is above the threshold Ta. If not, the respective lead does not exhibit a significant intensity reduction (410). Subsequently, the relative difference (H-L)/H is checked whether it is above the threshold Tr (412). If not, the respective lead does not exhibit a significant intensity reduction (414). Otherwise, as both the absolute and relative criteria are met, the reduction is determined as significant (416). Optionally, the relative difference check (412) may precede the absolute difference check (408). Optionally, the threshold Tr may be dependent on the absolute difference Ta. Optionally, the threshold Ta may be dependent on the relative difference Tr.

Plurality of Leads

In exemplary embodiments of the invention, in order to reach a reliable diagnosis, the significance of intensity reduction in a plurality of leads is determined.

Figure 5A:
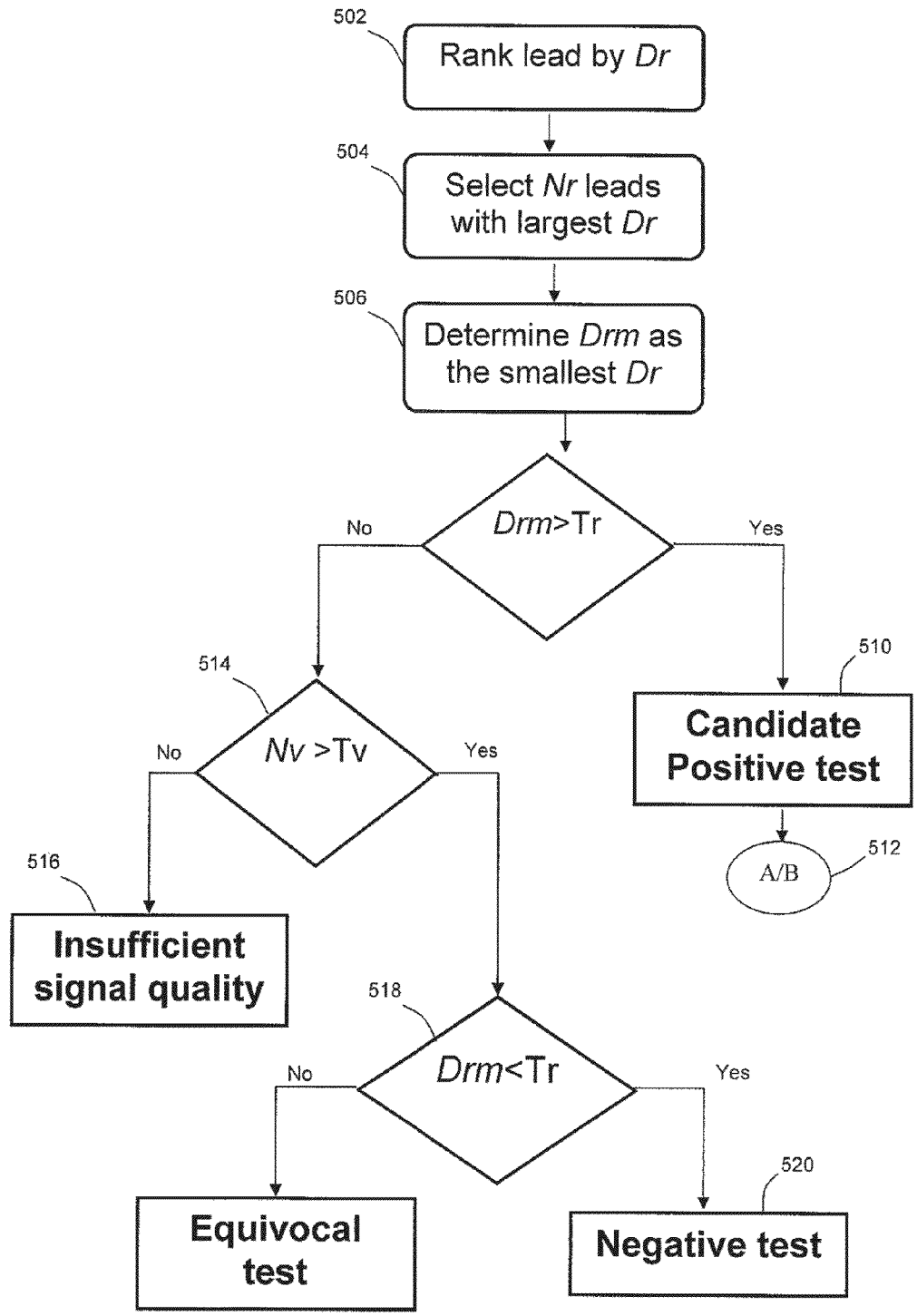
FIG. 5A. illustrates a flowchart for determining the significance of intensity reduction of a plurality of leads, in accordance with an exemplary embodiment of the invention.

FIGS. 5A and 5B illustrate a flowchart for determining the significance of intensity reduction of a plurality of leads, in accordance with two exemplary embodiments of the invention.

In an alternative interpretation, FIG. 5B illustrates an alternative flowchart for determining the significance of intensity reduction of a plurality of leads, in accordance with an exemplary embodiment of the invention.

In exemplary embodiments of the invention, the leads are ranked according to the relative difference of the intensity (Dr) (502). A group of Nr leads with the largest Dr is selected (504), and within the group the smallest Dr is selected, denoted as Drm (506).

In exemplary embodiments of the invention, Nr is 3. Optionally, Nr is 2. Optionally, Nr is larger than 3 such as 5. Optionally, Nr is an integral percentage of the number of leads or non-rejected leads, such as 30%.

Before further determinations, Drm is checked if it is larger that Tr, that is, whether the Dr values of the group of Nr leads with largest Dr satisfy the relative difference criterion. If the criterion is met, the test is a candidate for a significant test (510). Optionally the determination of intensity reduction proceeds to timing determinations according to FIG. 6 below. Optionally or alternatively, the determination is continued (512) according to FIG. 5B.

If the relative criterion is not met, and the number Nv of leads with valid (i.e. not rejected) signals is less than a sufficient minimal (Tv) (514) then the test signals are determined as of low quality for a reliable diagnosis (516). Otherwise, if there are sufficient number of leads with valid signals (at least Tv), while Drm still satisfies the relative difference criterion (518), the test is determined as equivocal, or ambiguous, and is a candidate for complementary determination, optionally with different qHF, to resolve the ambiguity. Otherwise the test is not significant (negative) (520), that is, ischemia is not diagnosed. Optionally, the threshold Tv is dependent on the number of leads with Dr above the threshold Tr.

In exemplary embodiments of the invention, the intensity reduction determination proceeds according to FIG. 5B.

Having a candidate for a significant test (510) the determination is continued, according to FIG. 5B (522), to verify if the number Ns of leads with significant intensity reduction is sufficient (at least Tsa) (524). If the number Ns is sufficient the test is a candidate for a significance test (526), and the determination is continued (528) according to FIG. 6 as described below. If the number Ns is not sufficient and the number Nv of leads with valid signals is less than a sufficient minimal (Tv) (530) then the test signals are determined as of low quality for a reliable diagnosis (532), as described above. Otherwise, if the number Ns of leads with significant intensity reduction is sufficient (at least Tsb) (534) the test is determined as ambiguous, as describe above. Else, the test is not significant (538), that is, ischemia is not diagnosed. Optionally, the threshold Tv is dependent on Ns.

In exemplary embodiments of the invention, the minimal number of valid leads Tv is 9. Optionally, Tv is 5. Optionally, Tv is 3. Optionally, Tv is a number between 2 and 12.

In exemplary embodiments of the invention, the first criterion for sufficient number of leads with significant reduction Tsa (5s4) is 5. Optionally, Tsa is 3. Optionally, Tsa is 7. Optionally, Tsa is between 3 and 11.

In exemplary embodiments of the invention, the second criterion for sufficient number of leads with significant reduction Tsb (534) is 3. Optionally, Tsa is 5. Optionally, Tsa is 7. Optionally, Tsa is between 2 and 11.

In exemplary embodiments of the invention, Tsa is equal or larger than Tsb.

Figure 6:
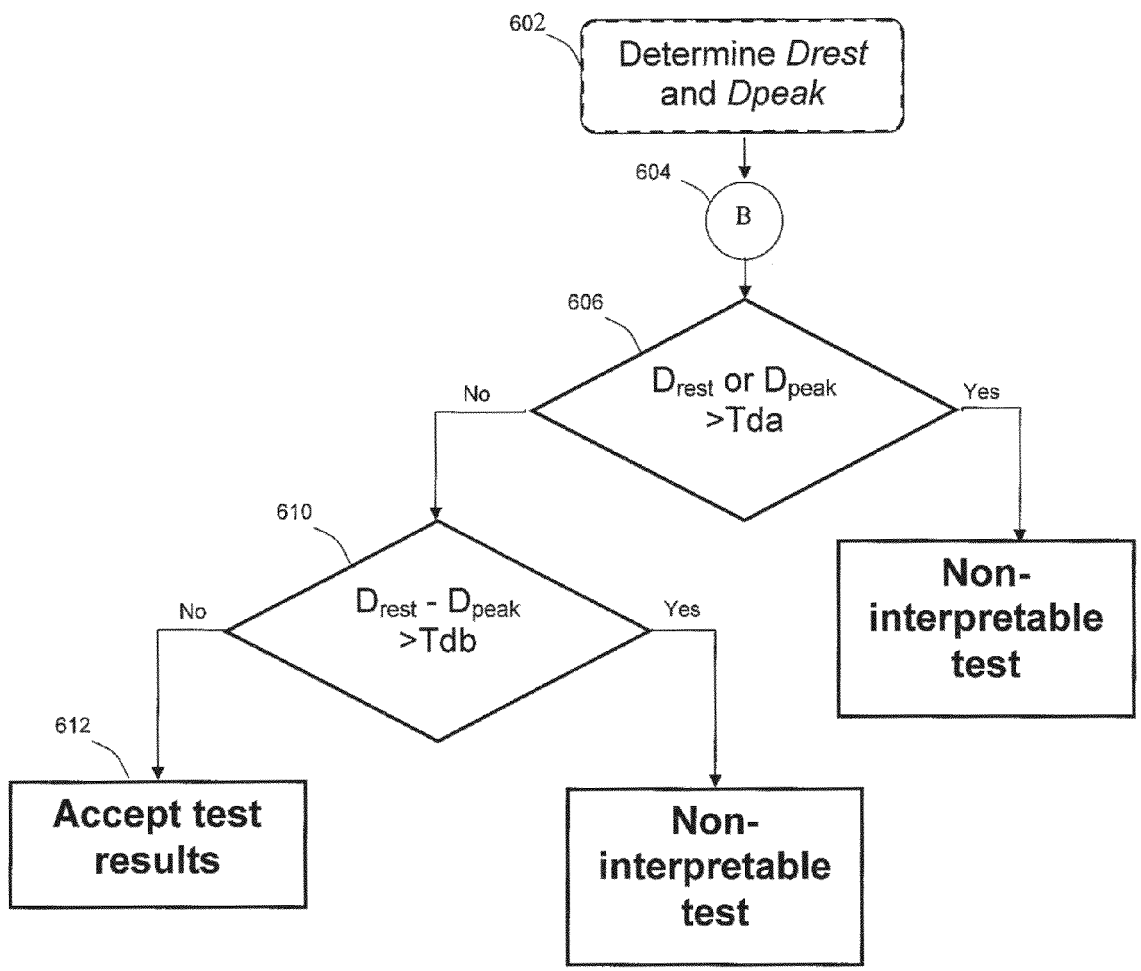
FIG. 6 illustrates a flowchart for determining whether the timing of the waveforms of HFQRS (or QRS) is reasonable physiologically, in accordance with an exemplary embodiment of the invention.

FIG. 6 illustrates a flowchart for determining whether the timing of the waveforms of HFQRS (or QRS) is reasonable physiologically, in accordance with an exemplary embodiment of the invention.

The duration of the HFQRS (or QRS) at rest (Drest) and at peak stress or heart rate (Dpeak) is determined (602). Optionally, the determination comprises a part of the QRS (or HFQRS) detection as described above.

Having a candidate for a significant test (526) the determination is continued, according to FIG. 6 (604), to verify if Drest or Dpeak are not too long (over a threshold Tda) (606). If the any of the durations is too long, the test is determined as non-interpretable, optionally due to the physiological reasoning. Otherwise, if the durations are less than Tda, the similarity of durations is determined, that is, whether the difference of the duration are small enough (below a threshold Tdb) (610). If the Drest and Dpeak are determine as similar then the test is determined as acceptable for diagnosis (612). Otherwise, if the durations are not similar enough (above Tdb) then the test is non-interpretable (optionally for physiological reasons).

In exemplary embodiments, the correlation between the QRS are peak exercise and rest is calculated. If the correlation is below a threshold Cq, the test is determined as non interpretable, optionally due to the physiological reasoning.

In exemplary embodiments of the invention, the correlation threshold Cq is 0.9. Optionally, Cq is 0.7. Optionally, Cq is 0.95. Optionally, Cq is between 0.7 and 1.

In exemplary embodiments of the invention, different leads are evaluated with different qHF, optionally with different threshold values and/or determination rules. Optionally, when combining the determinations of a plurality of leads, different leads have different weights in the combination.

In exemplary embodiments of the invention, once a significant intensity reduction was determined it may be further established or refined by correlating the determination with other quantifications qHF or features of the ECG and/or QRS and/or S-T and/or HFQRS. For example, following is a list of parameters known to respond response to ischemia, which may be used as primary or secondary considerations (depending on the decision making method):

(a) an RMS level of at least one HF QRS complex—this is HFQRS intensity (b) a standard deviation within an HF QRS complex—another measure of intensity (c) a kurtosis within an HF QRS complex—a measure for the presence of reduced amplitude zone (d) an entropy level within an HF QRS complex—a measure of flatness (e) an RMS level of the noise of at least one HF QRS complex—used to verify that a reduction was not missed due to noise (f) a signal-to-noise ratio of at least one HF QRS complex—used to exclude noisy leads, (g) a cross-correlation value of the HF QRS complex with a template waveform—to detect morphological changes, (h) a kurtosis within an envelope of an HF QRS complex—a measure for the presence of reduced amplitude zones (i) a central moment of any order within an envelope of an HF QRS complex, I added this to include any changes to HFQRS morphology (j) an entropy level within an envelope of an HF QRS complex—a measure of flatness (k) an envelope maximum over an HF QRS complex—another measure of intensity (l) an envelope width of an HF QRS complex—detects morphological changes (m) a cross-correlation value of the envelope of HF QRS complex with a template—again, to detect morphological changes Additional parameters include, a function of an envelope of an HF QRS complex, a function over a plurality of envelopes of HF QRS complexes, a kurtosis within an envelope of an HF QRS complex, a kurtosis over a plurality of envelopes of HF QRS complexes, a central moment of any order within an envelope of an HF QRS complex, a central moment of any order over a plurality of envelopes of HF QRS complexes, an entropy level within an envelope of an HF QRS complex, an entropy level over a plurality of envelopes of HF QRS complexes, an envelope maximum over an HF QRS complex, an envelope maximum over a plurality of HF QRS complexes, an envelope width of an HF QRS complex, an envelope width over a plurality of HF QRS complexes, a cross-correlation value of said envelope of HF QRS complex with a template and/or derivations of any one thereof.

Exemplary non-HF parameters include: QRS duration of at least one QRS complex, ST segment level of at least one QRST complex, Presence of upsloping ST segment in at least one QRS complex, Presence of downsloping ST segment in at least one QRS complex, Presence of horizontal ST segment in at least one QRS complex, QT interval in at least one QRS complex, QTc interval in at least one QRS complex, PR interval in at least one QRS complex, Electrical axis in at least one QRS complex, Heart rate, T-wave inversion in at least one QRS complex, T-wave peakedness in at least one QRS complex, T-wave abnormality in at least one QRS complex, Presence of atrial arrhythmias, Presence of ventricular arrhythmias, Presence of incomplete left bundle branch block, Presence of incomplete right bundle branch block, Presence of complete left bundle branch block, Presence of complete right bundle branch block, Presence of conduction blocks, Presence of P-wave abnormalities in at least one QRS complex, Presence of slurs or notches in at least one QRS complex, Presence of conduction abnormalities, Amplitude of at least one QRS complex, and Wolff-Parkinson-White syndrome.

Optionally, a component of the vector of secondary HF indices is a running average of a component of the vector of primary HF indices. Optionally, components of the vector of secondary HF indices are functions of:

(a) components of the first vector of primary HF indices calculated by the primary HF analyzer from a first high frequency (HF) range QRS complex received at a first time period and (b) components of a second vector of primary HF indices calculated by the primary HF analyzer from a second high frequency (HF) range QRS complex received at a second time period.

Optionally, a component of the vector of secondary ECG indices is a running average of a component of the vector of primary ECG indices.

Optionally, components of the vector of secondary ECG indices are functions of:

(a) components of the first vector of primary ECG indices calculated by the primary ECG indices analyzer from a the ECG received at a first time period and (b) components of a second vector of primary ECG indices calculated by the primary ECG indices analyzer from the ECG received at a second time period.

Optionally, the secondary HF indices provide an overall quantification of the high frequency QRS complex or complexes from which they are derived.

Optionally, the secondary HF analyzer detects all global and local minima of the RMS values. Optionally, the secondary ECG analyzer calculates the duration of the QRS complex at peak exercise. Optionally, the components of the vector of secondary ECG indices are functions of:

components of the first vector of primary ECG indices calculated by the primary ECG analyzer from a first QRST complex received at a first time period and components of a second vector of primary ECG indices calculated by the primary ECG indices analyzer from the ECG received at a second time period.

Optionally, values for the parameters mentioned above are determined in a clinical setting and used as part of a decision making process, for example, one base don weighted values or a rule based method. Optionally, the matching of various values to conditions is made using methods known in the art and stored in table and/or taught to physicians, optionally as a formula.

In an exemplary embodiment of the invention, a decision is made using various methods known in the art, for example, in one embodiment, the decision algorithm comprises a set of rules regarding the vector of primary indices, the vector of secondary HF indices, the vector of primary ECG indices and the vector of secondary ECG indices.

In another embodiment, the decision algorithm comprises a linear combination of the components of the vector of primary indices, the vector of secondary HF indices, the vector of primary ECG indices and the vector of secondary ECG indices.

In another embodiment, the decision algorithm comprises a nonlinear combination of the components of the vector of primary indices, the vector of secondary HF indices, the vector of primary ECG indices and the vector of secondary ECG indices.

In another embodiment, the decision algorithm comprises a decision tree that uses as input the components of the vector of primary indices, the vector of secondary HF indices, the vector of primary ECG indices and the vector of secondary ECG indices.

In another embodiment, the decision algorithm comprises a neural network that uses as input the components of the vector of primary indices, the vector of secondary HF indices, the vector of primary ECG indices and the vector of secondary ECG indices.

In exemplary embodiments of the invention, a non-stress ischemia is determined by intensity reduction as described above, or similar to as described above. For example, a patient at rest or in regular activities might have intermittent ischemic events.

In exemplary embodiments of the invention, the patient is monitored with ECG, or the ECG is recorded during normal activities and analyzed off-line (e.g. Holter recording). Optionally, the intensity reduction is evaluated and diagnosed from the online or off-line ECG recordings as described above. Optionally, some of the parameters such as qHF or thresholds are different from those of the stress exercise.

Apparatus

In exemplary embodiments of the invention, ECG are acquired by contact lead and/or implantable leads. Optionally, a standard and/or non-standard unit is used to obtain the voltage and/or current and/or phase of the signals. Optionally, the unit pre-processes and/or filters the signals, and/or calibrates them and/or amplifies them.

In exemplary embodiments of the invention, the signals are sampled by an analog-to-digital (A/D) converter (ADC) and read by a computer or computer system. Optionally, the ADC comprises hardware and/or software and/or firmware.

Optionally, the computer comprises software and/or hardware and/or firmware that performs the computations and mathematical derivations such as QRS detection, or alignment, or combination, or filtering or derivation of qHF, or performing of the rules and logic for intensity reduction, or other operations. Alternatively or additionally, other circuitry may be provided, for example, ASICs.

In exemplary embodiments of the invention, the computer system comprises one or more DSP and/or ASIC units and/or dedicated hardware such as a noise filter or high frequency filter.

HyperQ/HyperMaps

In exemplary embodiments of the invention, a suggestion for ischemia may be visualized by plotting the HFQRS along the scale of the test time (HyperQ in a HyperMap). Optionally, the plot is coded color and/or shades of gray for better visualization.

FIG. 7A schematically illustrates how the a HyperMap and the HyperMap derivation, in accordance with an exemplary embodiment of the invention.

In exemplary embodiments of the invention, an ECG QRS signal, or a representative QRS (702) as described above is filtered (704) to yield a HF QRS waveform or representative HF waveform (HPQRS) (706) as described above. Optionally, for a convenient visualization, the HFQRS is rotated (708) and the intensity is color and/or gray coded (710). A sequence of consecutive (with respect to test time) color/gray codes 710 is appended (712) to yield a chart of HF waveform intensities along the course of the test (714).

FIG. 7B schematically illustrates a HyperMap 720 of a normal patient in the course of a test, in accordance with an exemplary embodiment of the invention. The color/gray codes are inverted (negative) for improved clarity. HyperMap 720 exhibits a similar amplitude, visualized as width 722.

FIG. 7C schematically illustrates a HyperMap 730 of an ischemic patient in the course of a test, in accordance with an exemplary embodiment of the invention. The color/gray codes are inverted (negative) for improved clarity. HyperMap 730 exhibits varying intensity, that is, width between dark band 732. At the beginning of the test before a marked stress, the intensity is high (734). As the stress increases, the intensity decreases (736) to a minimal region (738) about the peak of the stress, and then decreases (740) as the patient relaxes. See FIG. 3 for a similar behavior and corresponding heart rate.

In this manner, the HyperMap can reveal an ischemic event during a test. Optionally, the test comprises a non-stress test. For example, intermittent supply-ischemia while the patient is monitored or off-line from the patient recorded ECG.

Possible Underlying Physiology

Without being limited to a particular theory, the following physiological theory may be useful in applying some embodiments of the invention.

When blood flow to a part of the heart is reduced, several changes occur, including changes in depolarization behavior and changes in conduction velocity. Possibly, inter-cell variability changes as well. In an exemplary embodiment of the invention, it is assumed that changes in conduction velocity cause a reduction in high frequency components and/or other changes in the HF signal (e.g., as averaged/combined over several heart beats or, in some embodiments, for a single heart beat).

In a particular embodiment of the invention, it is assumed that changes have a known behavior, for example, in stress, conduction velocity goes up with stress. When conduction velocity goes down due to pathology it may be expected to go down faster than if it is a natural reduction.

One potential problem with measuring these changes is that the measured ECG signal is a composite signal showing contributions of various parts of the heart overlaid. It is theorized that a reduction or reduced increase in conduction velocity during exercise in a cardiac area, will cause a relative reduction in the composite output signal or a reduction as compared to what would be expected from the patient (e.g., in comparison to other similar situations at which the patient or groups of patients are tested). Other changes in HF signals may also be visible, for example, using measures as described herein.

Exemplary Diagnostic Method

In an exemplary embodiment of the invention, the diagnostic method comprises looking for potential ischemic events and then determining if the events are likely to be ischemic events. This is in contrast to prior methods where the determination of ischemia was by measurement at pre-set points. Optionally, such measurement is also used in some embodiments of the invention.

In an exemplary embodiment of the invention, an ischemic event is detected by applying a local filter (e.g., one which has a width of 5 minutes, 2 minutes, 1 minute, 30 seconds, 10 seconds or smaller or intermediate values), which detects changes in HF signals which may indicate ischemia. An example of such a filter is a reduction in RMS. In other embodiments, a point of reference is dynamically selected, for example, maximum RMS and used as a reference. In an exemplary embodiment of the invention, this point of reference is selected on the basis of the signal, not the activity (e.g., point where maximum HF signal is found, not point of maximum stress). In other embodiments, a point may be selected which is a property of the diagnosis (e.g., maximum stress). It is noted that in some patients, a reduction in HF signals may appear before maximum stress is achieved and, in some cases, before maximum HF signal appears. This may have the form of a reduction in HF increase, as compared to what is expected under the conditions.

In an exemplary embodiment of the invention, after detecting a point which may be an ischemic event additional considerations are applied, for example, considerations which weaken the assumption or those which strengthen it. Optionally, the additional considerations veto the assumption the point is an ischemic event (e.g., based on ECG morphology).

An example of another additional consideration is an analysis at another point in time, for example, a repeated stress, or behavior during recovery. Increase in HF components during recovery or repetition of similar reduction at a similar stress level may be indicative of an ischemic event.

In some embodiments, once a potential ischemic event is found, other methods, ECG or not are used to further analyze the signal. Optionally or alternatively, ECG methods are used and specific filters are applied to those parts of the signal where an indication of ischemia was detected, for example, the raw signal or the averaged/combined signal.

An example of an additional consideration which may be used is using ST changes and/or angina. In one example, there is a threshold on ST changes (e.g., 2 mm) and a requirement for HFQRS reduction.

In an exemplary embodiment of the invention, stress is applied using various methods, such as exercise or drugs.

In an exemplary embodiment of the invention, drugs are used to validate the methods. For example, a drug which affects conduction velocity may be used to see if changes (increase or decrease) in conduction velocity affect the HF signal as expected. Alternatively or additionally, such drugs are used to set a baseline value for a patient, for using with absolute reduction or reduction relative to the baseline. Optionally, such drugs are used to determine a maximum conduction velocity for the patient and/or conditions and/or rates of conduction velocity changes. Optionally, conduction velocity is increased without stress, so that a baseline signal for what the HF signal might look like is generated.

Exemplary Applications

In one application, the methods described herein are used during a stress test (e.g., physical exercise, such as Bruce protocol, or pharmaceutical based). Optionally, the stress test is stopped when HF signal changes indicating ischemia are detected. Optionally, what is looked for is a reduction in HF signals when a maximum stress is achieved. It is noted, however, that reduction may be detected before or after the maximum stress using methods as described herein.

In other applications, the methods described herein are applied during the monitoring of an event, for example, to detect an effect of treatment or warn of side effects.

In one example, after or during an acute infarct, tPA or other clot treatment material may be administered. Optionally, the ECG signal is monitored to detect an increase in HF signals which indicate a return to normalcy. Alternatively or additionally, a reduction in HF values is found in parts of the signal that correspond to tissue that was electrically non-responsive due to ischemia and now becomes responsive.

Optionally, an ongoing infarct is diagnosed and/or treatment selected based in HF components in the signal, for example, based on a degree and/or type of ischemia detected. Optionally, a signal of the patient from before the ischemic/infarct event is used as a baseline. For example, a patient may have a normal variation in HF signal or may have a typical signal during resting or may have a particular temporal envelope during stress. Changes in any or all of these during an ischemic even can indicate the type and/or severity of the event, especially when used in conjunction with other diagnostic methods.

In an exemplary embodiment of the invention, the methods described herein are used as part of a monitoring program. Optionally, what is detected is a reduction in HFQRS intensity with respect to a reference value. The reference value is, for example, the maximal value during the time of measurement or a reference value obtained previously during a different measurement period.

In the example of a Holter, what may be detected is reductions in HF components at random times (e.g., due to vessel spasms). Alternatively or additionally, the reductions may progress over long periods of time, for example, tens of minutes or hours. Optionally, what is looked at is a reduction in size of HF component, for example, 20%, 30%, 40%, 45% or intermediate or greater values. Optionally, a normal standard is assessed and compared against.

In an exemplary embodiment of the invention, such monitoring is used to detect transient ischemic episodes or myocardial infarction. Optionally, such monitoring is applied to hi-risk patients and/or in a hospital stay (e.g., during treatment for other condition and/or treatment which increases ischemic risk).

In an exemplary embodiment of the invention, the monitoring is used to detect harmful mental stress (e.g., workplace stress). Optionally, when using a suitable Holter, or a journal, a user may mark the time as a time at which he felt stress, or indicate what type of event happened. Alternatively or additionally, a user may query the system (e.g., a Holter or other portable ECG device) as to whether an event the user is undergoing appears to have an effect on ischemia.

Optionally, such a monitoring device includes an ECG monitor, one or more ECG leads and a controller. Optionally, a memory for recording is provided. Optionally, the device includes a signaling unit (e.g., a speaker) for indicating to a user that an ischemic event is occurring and to slow down/take medication. Optionally, the device includes a user input (e.g., a button). Optionally, a device which measures both blood pressure and ECG is used. Optionally, the ECG signal is used as a trigger to measure blood pressure. Optionally, the device provides feedback based on real-time processing within 3 seconds, 10 seconds, 30 seconds, 1 minute, 5 minutes or intermediate times.

In some cases, monitoring can be used to detect supply ischemia. One example is detecting sleep apnea based on ischemic effects on cardiac tissue. Optionally, this is used to assist in deciding how aggressively to treat the apnea. Optionally or alternatively, nighttime monitoring is used to detect ischemic events less related to stress (as patient is inactive).

In an exemplary embodiment of the invention, methods as described herein are combined with a pacemaker and/or defibrillator. In one example, such methods can be used to signal to the pacemaker that additional cardiac output is required and/or that the heart is having an ischemic event, so the control of the heart should be changed.

In another example, the use of local electrodes in a pace maker, may allow a more exact determination of the location of an ischemic event or allow measuring the problematic area directly with less interference from signals form other parts of the heart. Optionally, a catheter or other part of pacemaker are used to directly measure changes in conduction velocity, for example, to provide a baseline or to allow erroneous signals to be rejected.

Optionally, the methods described herein are applied using a catheter, which, as noted, may perform local measurements, on a signal less affected by signals from other parts of the heart.

In an exemplary embodiment of the invention, the measurements as described herein are used as an input to other diagnostic methods (e.g., imaging studies), the methods being used as a basic screening; and/or used as a trigger for taking measurements (e.g., blood pressure or Doppler ultrasound).

In an exemplary embodiment of the invention, the measurements as described herein are used to improve the diagnostic and/or prognostic performance of other diagnostic methods (e.g., imaging studies).

Optionally, when applying a treatment, the methods as used herein are used to monitor the treatment, to guide changes in the treatment intensity/parameters and/or to determine if the treatment worked. In one example, the treatment is angioplasty and HF components may be measured before during and/or after treatment. Another example is bypass surgery, when an immediate effect of the bypass may be detected, as well as determining during surgery if additional bypasses may be required. Other examples are medications which open clots or which remove plaque (the time scales are generally different and so may be the times at which signals are compared).

Optionally, the signals and changes in signals are used as part of prognosis methods, for example, decision tables.

In an exemplary embodiment of the invention, a danger of arrhythmia is assessed based on changes in conduction velocity as shown by the HF signal. Optionally, this may be used even in patient with no current ischemia, for example, patients with damaged cardiac tissue which is incapable of reaching very high conduction velocities. Optionally, results from such patients are processed differently when searching for new ischemia, for example, by actively causing supply ischemia by reducing oxygenation levels (e.g., using a low oxygen gas), and thus affecting other cardiac tissue before maximum conduction velocity of the healthy or diseased tissue is reached. Such ischemia may also be used for diagnosis and/or baseline generation for other patients.

Sample Results/Diagnosis

Various studies have been carried out to show the effectiveness of HF analysis, using methods as described herein.

In a first study, not using the SNR method described herein, 25 patients (62±11 years) with an anamnesis of coronary heart disease were included in this study. All of the patients performed a symptom-limited Stress ECG test. High frequency 12 lead ECG was obtained using the HyperQ™ System (BSP Biological Signal Processing LTD, Tel Aviv, Israel). The index for ischemia was the relative change in intensity of the high frequency QRS components (HyperQ™) during the stress test. Conventional 12 lead ECG was acquired simultaneously. The sensitivity of both high frequency ECG and conventional ECG was determined by comparison with coronary angiography and intravascular ultrasound. Results of the stress tests were analyzed blindly to the outcome of coronary angiography.

The results were that 18 out of 25 patients (72%) with known coronary heart disease showed a significant coronary stenosis in one (72%) or two (28%) arteries. The HyperQ™ system detected 11 out of these 18 patients with a hemodynamic relevant stenosis. In contrast, conventional ST-T changes indicating ischemia were detected in 5 out of these 18 patients. The HyperQ™ showed a clear increase in sensitivity relative to conventional 12-lead stress ECG (72% vs. 27%). The specificity of the HyperQ™ was approximately 85%.

In another study, patients undergoing exercise myocardial perfusion imaging (MPI) using stress single-photon emission computed tomography and using the methods described herein were compared to conventional electrocardiographic (ECG) analysis using MPI as the gold standard. Exercise MPI was performed in 95 consecutive patients (72 men and 23 women; age, 62 F 11 years) and was used as the gold standard for ischemia. Patients were eligible if they were willing to provide informed consent, had an interpretable ECG, and were able to walk on the treadmill. Exclusion criteria included cardiac pacemaker placement, atrial fibrillation at the time of testing, complete left or right bundle-branch block, interventricular conduction defect, and ST segment depression of at least 1 mm at rest before exercise testing. Conventional exercise ECG recording was combined with high-resolution ECG acquisition, which was digitized and analyzed using a HyperQ system (BSP Ltd, Tel Aviv, Israel). The software extracted the high-frequency components of the QRS complex (HyperQ), classified the HyperQ data from the 12 leads, and discarded those leads that had a very low signal-to-noise ratio. The remaining leads with sufficient signal-to-noise ratio were examined for the presence of reduction in HyperQ intensity. Leads that exhibited relative reduction greater than 40% were considered indicative of ischemia and were visually marked. The HyperQ test was considered positive if at least 2 leads were indicative of ischemia. The system provided a quantitative index of ischemia based on the HyperQ response to exercise. It is important to note that analysis of HyperQ data was computerized, resulting in an automated, objective, and quantitative assessment of the data with no inter-observer and intra-observer variability. ST segments were considered abnormal if there was at least 1 mm of horizontal or downsloping depression 80 milliseconds after the J point for at least 3 consecutive beats in 2 contiguous leads. Stress testing was performed with the use of a treadmill (the Bruce protocol). Each patient was studied under fasting conditions. Patients were asked to discontinue their anti-anginal medications 24 hours before testing and their b-blocker medications 48 hours before testing. Imaging protocol and image analysis were performed according to an acceptable protocol. Perfusion defects were analyzed visually and semi-quantitatively.

The analysis was possible in 85 patients, 33 of whom exhibited MPI ischemia. Stress-induced ischemia was characterized by a reduction in HyperQ intensity, whereas the normal HyperQ response was characterized by either a constant or an increase in intensity. Ischemic HyperQ response was found in 25 of the 33 ischemic subjects and in 8 of the 52 non-ischemic subjects. Four subjects exhibited ST depression at rest and 17 subjects exhibited inconclusive ST changes. Significant ST changes were detected in 15 of 27 patients with MPI ischemia and in 19 of 50 patients without MPI ischemia. The HyperQ index of ischemia exhibited higher sensitivity relative to conventional ST analysis (76% vs 59%; P b 0.01), improved specificity (85% vs 57%; p<0.001), higher positive predictive and negative values (76% vs 49% [p<0.01] and 85% vs 70% [p<0.05], respectively), and higher accuracy (81% vs 58%; p<0.001).

In another study, which used cross-correlation as an analysis technique, the methods were tested detecting ischemia caused by short intra-coronary balloon occlusions and compared to conventional ECG interpretation.

The methods were: High resolution ECG was acquired and the HyperQ signal representing HF-QRS data derived using the HyperQ™ System (BSP, Israel) in 34 patients undergoing coronary angioplasty (16 LAD, 10 RCA, 8 LCX). Two epochs were defined for the first balloon occlusion: (i) 60 s baseline before inflation and (ii) immediately before deflation. Changes in the HyperQ signal and in the ST level were measured before deflation relative to baseline. Changes in the HyperQ signal were quantified by a cross-correlation technique. HyperQ signal changes were considered significant if larger than three times the standard deviation of the signal during baseline.

The results were: Occlusion duration was 68±16 s. Typical HyperQ response to occlusion included marked changes in both the intensity and morphological features of the HyperQ signal, manifested in reduction of the correlation function. Significant HyperQ changes were found in 32 patients (94%). In contrast, significant ST changes were observed in 15 patients (44%, p<0.01).

In another study, high-resolution ECG was acquired (HyperQ™ System, BSP, Israel) during clinically indicated exercise test in 616 consecutive patients (age 57±11 years, 404 men). HFQRS data were evaluated automatically using computerized analysis. Patients with evidence of ischemia in exercise ECG or HFQRS data were referred for follow-up imaging tests (stress echocardiography, SPECT perfusion imaging, computed tomography of the coronary arteries, or angiography). The follow-up imaging tests were used as the gold standard for presence of ischemic heart disease (IHD).

The results were that in 511 patients, no evidence of ischemia in the exercise test was observed and thus they were not referred for follow up testing. In 105 patients, either (or both) positive exercise ECG or HFQRS result was observed. Of the first 50 patients who completed the follow up tests, 36 had unequivocal exercise ECG (follow-up tests indicated IHD in 10 patients). HFQRS analysis was unequivocal in 32 patients (follow-up tests indicated IHD in 8 patients). HFQRS analysis resulted in significantly higher diagnostic performance for detecting IHD using exercise testing (table, below).

|  | Exercise ECG | HFQRS analysis |
| --- | --- | --- |
| No. of patients | 36 | 32 |
| Sensitivity | 60% (6/10) | 75% (6/8) |
| Specificity | 54% (14/26) | 92% (22/24)** |
| Pos. predictive value | 33% (6/18) | 75% (6/8)* |
| Neg. predictive value | 78% (14/18) | 92% (22/24) |
| Accuracy | 56% (20/36) | 88% (28/32)** |

*p < 0.05,
**p < 0.005

In another study, the methods were: exercise myocardial perfusion SPECT (MPS) was performed in 133 consecutive patients (age: 63±12 years, 100 men) and used as the gold standard for ischemia. Patients with bundle branch blocks (n=19) or inconclusive MPS (n=5) were excluded. Conventional ECG was combined with high resolution ECG acquisition that was digitized and analyzed using the HyperQ™ System (BSP, Tel Aviv, Israel). The relative HFQRS intensity change during exercise was used as an index of ischemia. The results were: HFQRS analysis was possible in 105 patients of whom 22 exhibited MPS ischemia (4 patients excluded due technical reasons). The HFQRS index of ischemia was found more sensitive than the conventional ST analysis (77% vs 43%, p<0.05, see table) with comparable specificity (66% vs 57%, p=NS). In women, HFQRS analysis resulted in improved specificity relative to conventional ECG (70% vs 33%, p<0.05). In patients with inconclusive ST changes, HFQRS analysis correctly identified 17/21 patients. The results may be used to show that HFQRS analysis was more sensitive in detecting stress-induced ischemia and exhibited improved specificity in women. Optionally, women are selected in greater probability for testing than men. Alternatively or additionally, results in women are given a higher weight than in men, when diagnosing.

|  | Number of subjects | HFQRS Sensitivity | ST Sensitivity | HFQRS Specificity | ST Specificity |
| --- | --- | --- | --- | --- | --- |
| All patients | 105 | 77%* (17/22) | 43% (9/21) | 66% (55/83) | 57% (37/65) |
| Women | 29 | 83% (5/6) | 75% (3/4) | 70%* (16/23) | 33% (5/15) |
| Inconclusive ECG | 21 | 100% (2/2) | NA | 79% (15/19) | NA |

In another study, SNR methods were not used. The methods were, as follows. Exercise myocardial perfusion SPECT (MPS) was performed in 885 consecutive patients (643 male) and used as the gold standard for ischemia. Conventional exercise ECG recording was combined with high resolution ECG acquisition, which was digitized and analyzed using the HyperQ™ System (BSP, Israel). The relative intensity change of high frequency QRS components (HyperQ™) during exercise was used as an index of ischemia. Logistic regression was used to assess incremental diagnostic value of HyperQ data over conventional ECG. The results were that moderate to severe MPS ischemia was found in 36 patients. The HyperQ index of ischemia was more sensitive than conventional analysis (78% vs 56%, p<0.01) with similar specificity (74% vs 78%, p=ns). The HyperQ index offered a significant incremental diagnostic value over clinical and stress test data.

General

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features. Alternatively and additionally, portions of the invention described/depicted as a single unit may reside in two or more separate physical entities which act in concert to perform the described/depicted function. Alternatively and additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. The scope of the invention is limited only by the following claims.

All publications and/or patents and/or product descriptions cited in this document are fully incorporated herein by reference to the same extent as if each had been individually incorporated herein by reference or if they were reproduced in full herein.

The invention claimed is:

1. A method for analyzing ECG signals, comprising:
   (a) providing at least one ECG signal recorded from a body;
   (b) having a computer determine the value of at least one time-varying parameter of a high frequency band of said ECG signal; and
   (c) having a computer generate an alert responsive to a decision algorithm comprising a set of rules involving a combination of:
      an instant variation of the time-varying parameter value during a test, wherein said instant variation is a change in the parameter value in comparison to the parameter value at a short time before; and
      an analysis of a T-wave abnormality in at least one QRS complex in a low-frequency component of said ECG signal,
   wherein:

said analysis of said low-frequency component of said ECG signal is performed in addition to any alignment of high frequency signals from said high frequency band of said ECG signal; and said alert comprises indicating ischemia.

2. A method according to claim 1 in which said analysis of a T-wave abnormality comprises detecting a T-wave inversion.

3. A method according to claim 1 in which said analysis of a T-wave abnormality comprises detecting a T-wave peakedness.

4. A method according to claim 1 in which said analysis of said low-frequency component of said ECG signal comprises detecting an ischemic event.

5. A method according to claim 1, wherein the ECG signal is sampled from a plurality of leads.

6. A method according to claim 5, wherein a lead with a high level of noise is discarded from the analysis.

7. A method according to claim 1, wherein said analyzing ECG signals comprises analyzing ECG signals in a monitoring setting.

8. A method according to claim 1, wherein said analyzing ECG signals comprises analyzing ECG signals in a stress-testing setting.

9. A method according to claim 1, and further comprising at least one more analysis of said low-frequency component of said ECG signal selected from a group consisting of:
QRS duration of at least one QRS complex;
level of an ST segment of at least one QRST complex;
presence of an up-sloping ST segment in at least one QRS complex;
presence of a down-sloping ST segment in at least one QRS complex;
presence of a horizontal ST segment in at least one QRS complex;
QT interval duration in at least one QRS complex;
QTc interval duration in at least one QRS complex; and
PR interval duration in at least one QRS complex.

10. A method according to claim 1 in which said set of rules involves at least one of following: a vector of primary indices, a vector of secondary HF indices, a vector of primary ECG indices and a vector of secondary ECG indices.

11. Apparatus for ECG signal analysis, comprising:
(a) an input for an ECG signal;
(b) a high-frequency band extractor which extracts a high frequency (HF) band from said signal;
(c) a filter configured to analyze said HF band and detect an instant variation, wherein said instant variation is a change in value of a time-varying parameter in comparison to the parameter value at a short time before;
(d) a processor configured to perform analysis of a T-wave component in at least one QRS complex in a low frequency component of said ECG signal, producing at least one physiological consideration; and
(e) an output which generates an output signal responsive to a decision algorithm comprising a set of rules involving a combination of the instant variation and the analysis of the low frequency component, wherein said analysis of said low-frequency component of said ECG signal is performed in addition to any alignment of high frequency signals from said high frequency band of said ECG signal.

12. Apparatus according to claim 11 in which said analysis of said T-wave abnormality comprises detecting a T-wave inversion.

13. Apparatus according to claim 11 in which said analysis of said T-wave abnormality comprises detecting a T-wave peakedness.

14. Apparatus according to claim 11 in which said analyzing ECG signals comprises detecting an ischemic event.

15. Apparatus according to claim 11, mounted as a wearable ECG monitor.

16. Apparatus according to claim 11, configured as a part of an implantable device.

17. Apparatus according to claim 11, configured as a part of an exercise stress test system.

18. Apparatus according to claim 11, comprising a memory adapted to store a reference value from a different session.

* * * * *